United States Patent [19]

Yamada et al.

[11] Patent Number: 5,237,100
[45] Date of Patent: Aug. 17, 1993

[54] SUBSTITUTED BENZYLCYCLOALKENYLAMINES AND CARBAMOYLHALIDE INTERMEDIATES THEREFOR

[75] Inventors: Yasuo Yamada; Junichi Saito; Tatsuo Tamura; Shinji Sakawa, all of Tokyo, Japan

[73] Assignee: Nihon Bayer Agrochem K.K., Tokyo, Japan

[21] Appl. No.: 873,494

[22] Filed: Apr. 23, 1992

Related U.S. Application Data

[60] Continuation of Ser. No. 455,872, Dec. 19, 1989, abandoned, which is a continuation of Ser. No. 286,590, Dec. 19, 1988, abandoned, which is a division of Ser. No. 130,248, Dec. 8, 1987, Pat. No. 4,857,556, which is a continuation of Ser. No. 849,992, Apr. 10, 1986, abandoned, which is a continuation of Ser. No. 555,868, Nov. 28, 1983, abandoned.

[30] Foreign Application Priority Data

Dec. 3, 1982 [JP] Japan .............................. 57-211241

[51] Int. Cl.$^5$ ............................................ C07C 211/40
[52] U.S. Cl. ...................................... 564/384; 564/391
[58] Field of Search ................................ 564/384, 391

[56] References Cited

U.S. PATENT DOCUMENTS

| 3,592,805 | 7/1971 | Szabo et al. | 564/384 X |
|---|---|---|---|
| 3,660,434 | 5/1971 | Martin et al. | 564/29 X |
| 3,701,807 | 10/1972 | Chupp | 260/553 A |
| 3,761,241 | 9/1973 | Chupp | 71/120 |
| 3,888,928 | 6/1975 | Willis et al. | 564/391 X |
| 4,127,673 | 11/1978 | Yamada et al. | 424/322 |
| 4,216,228 | 8/1980 | Yamada et al. | 564/29 X |
| 4,487,783 | 12/1984 | Grohe et al. | 564/26 X |

FOREIGN PATENT DOCUMENTS

| 376 | 1/1979 | European Pat. Off. | |
| 2037616 | 2/1972 | Fed. Rep. of Germany | 564/57 |
| 2732257 | 4/1981 | Fed. Rep. of Germany | |
| 90222 | 8/1978 | Japan | 514/595 |
| 32417 | 4/1981 | Japan | 514/598 |

*Primary Examiner*—Richard L. Raymond
*Attorney, Agent, or Firm*—Sprung Horn Kramer & Woods

[57] ABSTRACT

Substituted benzylcycloalkenylurea derivatives of the formula (I)

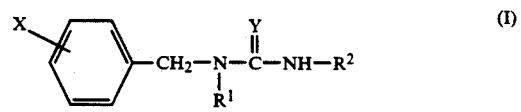

wherein X represents a halogen atom or a lower alkyl group,
Y represents an oxygen atom or a sulfur atom,
$R^1$ represents a cycloalkenyl group and
$R^2$ represents a lower alkyl group, a cycloalkyl group, a benzyl group or a phenyl group optionally substituted by 1 to 5 substituents selected from the group consisting of a hydroxyl group or a lower alkoxy group and their use as fungicides. They can be synthesized, for example, by reacting of a substituted benzyl-cycloalkenylamine with an isocyanate or by reacting of a carbamoyl halide with an amine. The starting material, the substituted benzyl-cycloalkenyl amines, are also new.

11 Claims, No Drawings

SUBSTITUTED BENZYLCYCLOALKENYLAMINES AND CARBAMOYLHALIDE INTERMEDIATES THEREFOR

This application is a continuation of U.S. application Ser. No. 455,872, filed Dec. 19, 1989, now abandoned, which is a continuation of 286,590, filed Dec. 19, 1988, now abandoned, which is a division of U.S. Ser. No. 130,248, filed Dec. 8, 1987, now U.S. Pat. No. 4,857,556, which is a continuation of U.S. Ser. No. 849,992, filed Apr. 10, 1986, abandoned, which is a continuation of U.S. Ser. No. 555,868, filed Nov. 28, 1983, now abandoned.

This invention relates to novel substituted benzylcycloalkenyl-urea derivatives, their intermediates, processes for the production of said derivatives and said intermediates, and agricultural or horticultural fungicides. It is already known that certain N-(1-cycloalken-1-yl) ureas and thioureas, such as, for example, N-benzyl-N-cyclohexen-1-yl-N'-phenyl urea, and N-cyclohexen-1-yl-N-methyl-N'-phenyl urea, have herbicidal and/or fungicidal properties (compare U.S. Pats. No. 3,701,807 and 3,761,241). The preparation and the use as fungicides of other N-cycloalkyl-N-benzyl-N'-phenyl urea derivatives are known (compare German Pat. No. 2,732,257).

New substituted benzyl-cycloalkenylurea derivatives of the following formula (I)

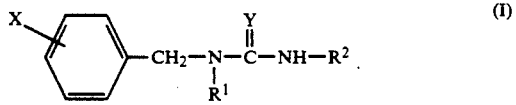

wherein X represents a halogen atom or a lower alkyl group;
  Y represents an oxygen atom or a sulfur atom;
  $R^1$ represents a cycloalkenyl group, and
  $R^2$ represents a lower alkyl group, a cycloalkyl group, a benzyl group or a phenyl group optionally substituted by 1 to 5 substituents selected from the group consisting of a hydroxyl group or a lower alkoxy group, have been found.

It has furthermore been found that the new substituted benzyl-cycloalkenylurea derivatives of the formula (I)

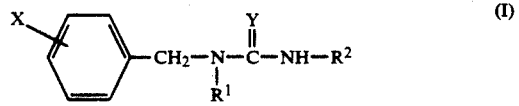

wherein X represents a halogen atom or a lower alkyl group;
  Y represents an oxygen atom or a sulfur atom;
  $R^1$ represents a cycloalkenyl group, and
  $R^2$ represents a lower alkyl group, a cycloalkyl group, a benzyl group or a phenyl group optionally substituted by 1 to 5 substituents selected from the group consisting of a hydroxyl group or a lower alkoxy group, are obtained by a process in which
  i) a substituted benzyl-cycloalkenylamine of the formula (II)

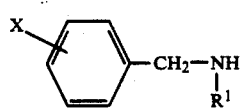

wherein X and $R^1$ are as defined above is reacted with an isocyanate of the formula (III)

$$R^2-N=C=Y \qquad (III)$$

wherein Y and $R^2$ are as defined above, if appropriate in the presence of a diluent, or
  ii) a carbamoyl halide of the formula (IV)

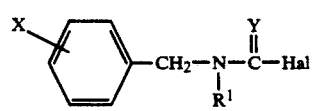

wherein X, Y and $R^1$ are as defined above and Hal represents a halogen atom, is reacted with an amine of the formula (V)

$$H_2N-R^2 \qquad (V)$$

wherein $R^2$ is as defined above, if appropriate in the presence of a diluent and if appropriate in the presence of an acid binder.

It has furthermore been found that the new substituted benzyl-cycloalkenylurea derivatives of the formula (I) have powerful fungicidal properties. They can be used as agricultural or horticultural fungicides. The substances according to the invention thus represent an enrichment of the art.

Formula (I) provides a general definition of the substituted benzyl-cycloalkenylurea derivatives according to the invention. Preferred compounds of the formula (I) are those in which
  X represents a halogen atom or a lower alkyl group with 1 to 6 carbon atoms,
  Y represents an oxygen atom or a sulfur atom,
  $R^1$ represents a cycloalkenyl group with 5 to 7 carbon atoms and
  $R^2$ represents a lower alkyl group with 1 to 6 carbon atoms, a cycloalkyl group with 5 to 8 carbon atoms, a benzyl group or a phenyl group optionally substituted by 1 to 5 of the same or different substituents selected from the group consisting of hydroxyl and an alkoxy group with 1 to 4 carbon atoms.

Particularly preferred compounds of the formula (I) are those in which
  X represents fluorine, chlorine, bromine, iodine, methyl, ethyl, n-propyl, iso-propyl, n-butyl, sec.-butyl, isobutyl or tert.-butyl,
  $R^1$ represents 2-cyclopenten-1-yl, 3-cyclopenten-1-yl, 2-cyclohexen-1-yl, 3-cyclohexen-1-yl, 2-cyclohepten-1-yl, 3-cyclohepten-1-yl and
  $R^2$ represents methyl, ethyl, n-propyl, iso-propyl, n-butyl, sec.-butyl, iso-butyl, tert.-butyl, cyclopentyl, cyclohexyl, cycloheptyl, cyclooctyl, benzyl, phenyl optionally substituted by 1 or 2, same or different substituents selected from hydroxyl, methoxy, ethoxy, n-propoxy and iso-propoxy.

If, for example N-(2-cyclohexen-1-yl)-N-(4-chloro-benzyl)amine and methylisocyanate are used as starting substances, the course of the reaction in process i) according to the invention can be represented by the following equation:

Cl—⟨C₆H₄⟩—CH₂—NH(cyclohexenyl) + CH₃—N=C=O ⟶

Cl—⟨C₆H₄⟩—CH₂—N(cyclohexenyl)—CO—NH—CH₃

If, for example, N-4-bromobenzyl-N-(2-cyclopenten-1-yl) carbamoyl-chloride and aniline are used as starting substances the course of the reaction in process ii) according to the invention can be represented by the following equation:

Br—⟨C₆H₄⟩—CH₂—N(cyclopentenyl)—CO—Cl + H₂N—⟨C₆H₅⟩ $\xrightarrow{\text{acid binder}}_{-HCl}$ Br—⟨C₆H₄⟩—CH₂—N(cyclopentenyl)—CO—NH—⟨C₆H₅⟩

The substituted benzyl-cycloalkenyl-amines of the formula (II) required as starting materials for process i) according to the invention are new. This invention also relates to these new intermediates of the formula (II). These intermediates may be produced, for example, by the following known processes:

Process a)

A process for producing a substituted benzylcycloalkenylamine of the above formula (II) which is characterized by reacting a substituted benzylamine of the formula:

$$X-\text{C}_6\text{H}_4-\text{CH}_2-\text{NH}_2 \quad \text{(VI)}$$

wherein X is as defined above with a compound of the formula:

$$R^1-\text{Hal} \quad \text{(VII)}$$

wherein $R^1$ and Hal are as defined above or

Process b)

A process for producing a substituted benzylcycloalkenylamine of the above formula (II) which is characterized by reacting a substituted benzyl halide of the formula:

$$X-\text{C}_6\text{H}_4-\text{CH}_2-\text{Hal} \quad \text{(VIII)}$$

wherein X and Hal are as defined above with a cycloalkenylamine of the formula:

$$R^1-\text{NH}_2 \quad \text{(IX)}$$

wherein $R^1$ is as defined above. Both processes a) and b) can be carried out if appropriate in presence of a diluent and in the presence of an acid binder at temperatures between about $-20°$ C. and the boiling point of the reaction mixtures, preferably between $0°$ C. and $100°$ C.

Specific examples of the starting material of the formula (II) are: N-4-chlorobenzyl-2-cyclopenten-1-ylamine, N-4-bromobenzyl-2-cyclopenten-1-ylamine, N-4-methylbenzyl-2-cyclopenten-1-ylamine, N-4-chlorobenzyl-2-cyclohexene-1-ylamine, N-4-bromobenzyl-2-cyclohexene-1-ylamine, N-4-methylbenzyl-2-cyclohexen-1-ylamine, N-4-chlorobenzyl-3-cyclopenten-1-ylamine, N-4-bromobenzyl-3-cyclopenten-1-ylamine, N-4-chlorobenzyl-3-cyclohexen-1-ylamine, N-4-methylbenzyl-3-cyclohexen-1-ylamine, N-4-chlorobenzyl-2-cyclohepten-1-ylamine.

The isocyanates of the formula (III) required as starting materials for process i) according to the invention are generally well-known compounds.

Specific examples of the isocyanate starting materials, of the formula (III) are methyl isocyanate, ethyl isocyanate, propyl isocyanate, n-butyl isocyanate, cyclohexyl isocyanate, phenyl isocyanate, 3-methoxyphenyl isocyanate, isopropyl isocyanate, ethyl isothiocyanate, phenyl isothiocyanate, n-butyl isothiocyanate, benzyl isothiocyanate, 3-hydroxyphenyl isocyanate, 4-hydroxyphenyl isocyanate, and 4-methoxyphenyl isocyanate.

Formula (IV) provides a general definition of the carbamoyl halides required as starting substances for process ii) according to the invention. They can be obtained by known analogous processes.

Specific examples of the carbamoyl halide starting materials of the formula (IV) are
N-4-chlorobenzyl-N-(2-cyclopenten-1-yl)carbamoyl chloride,
N-4-bromobenzyl-N-(2-cyclopenten-1-yl)carbamoyl chloride,
N-4-methylbenzyl-N-(2-cyclopenten-1-yl)carbamoyl chloride,
N-4-chlorobenzyl-N-(2-cylohexen-1-yl)carbamoyl chloride,
N-4-bromobenzyl-N-(2-cyclohexen-1-yl)carbamoyl chloride,
N-4-methylbenzyl-N-(2-cyclohexen-1-yl)carbamoyl chloride,
N-4-chlorobenzyl-N-(3-cyclopenten-1-yl)carbamoyl chloride, N-4-bromobenzyl-N-(3-cyclopenten-1-yl)carbamoyl chloride,
N-4-chlorobenzyl-N-(3-cyclohexen-1-yl)carbamoyl chloride,
N-4-methylbenzyl-N-(3-cyclohepten-1-yl)carbamoyl chloride,
N-4-chlorobenzyl-N-(2-cyclohepten-1-yl)carbamoyl chloride,
as well as the bromides corresponding to the above chlorides, and the thiocarbamoyl halides corresponding to the above carbamoyl halides, such as thiocarbamoyl chlorides and bromides.

Specific examples of the amine starting materials of the formula (V) required for process ii) according to the invention are the well-known amines methylamine, athylamine, propylamine, n-butylamine, cyclohexylamine, aniline, 3-methoxyaniline, isopropylamine, m-aminophenol. p-aminophenol, and 4-methoxyaniline.

Possible diluents for the reaction according to the invention in process i) include water; aliphatic, alicyclic and aromatic hydrocarbons (optionally chlorinated) such as hexane, cyclohexane, petroleum ether, ligroin, benzene, toluene, xylene, methylene chloride, chloroform, carbon tetrachloride, ethylene chloride and trichloroethylene, chlorobenzene etc.; ethers such as diethyl ether, methyl ethyl ether, di-isopropyl ether, dibutyl ether, propylene oxide, dioxane, tetrahydrofuran etc.; ketones such as acetone, methyl ethyl ketone, methyl iso-propyl ketone, methyl iso-butyl ketone etc.; nitriles such as acetonitrile, propionitrile, acrylonitrile etc.; esters such as ethyl acetate, amyl acetate etc.; acid amides such as dimethylformamide, dimethylacetamide etc.; sulfones and sulfoxides such as dimethylsulfoxide, sulfolane etc.; and bases such as pyridine etc.

The process i) of this invention may be practiced over a wide range of temperatures. Generally, it is carried out at a temperature between about −20° C. and the boiling point of the reaction mixture, preferably between about 0° C. and about 100° C. Although the reaction is desirably carried out at normal pressure, it is also possible to operate under elevated or reduced pressure.

The process ii) according to the invention may be practiced employing an inert solvent or diluent similar to the above-mentioned, thereby obtaining the desired product of high purity in a high yield.

Further, the above reaction ii) may be carried out in the presence of an acid binder. As such an acid binder, there may be mentioned commonly employed hydroxides, carbonates, bicarbonates, alkanolates, etc., of alkali metals, tertiary amines such as triethylamine, diethylaniline, pyridine, etc.

The above process ii) may be practiced over a wide range of temperatures. Generally, it is carried out at a temperature between about −20° C. and about the boiling point of the reaction mixture, preferably between about 0° C. and about 100° C. Although the reaction is desirably carried out at normal pressure, it is also possible to operate under elevated or reduced pressure.

Where a compound of the formula (I) wherein $R^2$ is a hydroxy-substituted phenyl group is desired, the above process i) is preferred.

In the process a) for the production of the new compounds of the formula (II) of this invention as illustrated above, specific examples of the benzylamine starting materials, of the formula (VI) are the known benzylamines 4-chlorobenzylamine, 4-bromobenzylamine, 4-methylbenzylamine, etc.

Specific examples of the other starting material of the formula (VII) include 3-chloro (or bromo)-cyclopentene, 3-chloro (or bromo)-cyclohexene, 4-chloro (or bromo)-cyclopentene, 4-chloro (or bromo)-cyclohexene, 3-chloro (or bromo)-cycloheptene, etc.

In the process b) for the production of the new compounds of the formula (II) of this invention as illustrated above, specific examples of the substituted benzyl halide starting material of the formula (VIII) include 4-chlorobenzyl chloride, 4-bromobenzyl chloride, 4-methylbenzyl chloride etc., as well as the bromides corresponding to the chlorides. Specific examples of the other starting material, the cylcoalkenylamines of the formula (IX), include 2-cyclopenten-1-ylamine, 2-cyclohexene-1-ylamine, 3-cyclopenten-1-ylamine, 3-cyclohexen-1-ylamine, 2-cyclohepten-1-ylamine, etc.

The above processes a) and b) may be practiced employing an inert solvent or diluent similar to the above-mentioned in processes i) and ii), thereby obtaining the desired product of high purity in a high yield.

Furthermore, the above processes a) and b) may be carried out in the presence of an acid binder similar to the above-mentioned.

The above processes a) and b) may be practiced over a wide range of temperatures. Generally, the reaction is carried out at a temperature between −20° C. and the boiling point of the reaction mixture, preferably between about 0° C. and about 100° C. Although the reaction is desirably carried out at normal pressure, it is also possible to operate under elevated or reduced pressure.

The novel subsituted benzyl-cycloalkenylurea derivatives of the above formula (I) have excellent agricultural or horticultural fungicidal activity.

Furthermore, the compounds of the formula (I) of this invention may be easily produced. Because of their urea (thiourea) backbone, the nitrogen atom at the 1-position carrying a substituted benzyl group and a cycloalkenyl group having 5-7 carbon atoms, especially a 2-(or 3-) cycloalken-1-yl group, and the nitrogen atom at the 3-position carrying $R^2$ as defined above, these compounds manifest an agricultural or horticultural fungicidal effect, particularly an extremely remarkable controlling effect on rice sheath blight caused by Pellicularia sasakii.

Furthermore, it has also been discovered that the compounds of the formula (I) of this invention can manifest a satisfactory controlling effect on damping-off of vegetables caused by Rhizoctonia solani.

The active compounds of this invention may be effectively employed against pathogenic fungi parasitizing the above-ground parts of plants, pathogenic fungi attacking plants through soil to cause tracheomycosis, seed-borne causative pathogenic fungi and soil-borne causative pathogenic fungi.

Further, since these compounds are of only low toxicity to warm-blooded animals and have good compatibility with higher plants, that is, do not show phytotoxicity to crop plants at concentrations usually employed, they may be quite conveniently employed against plant diseases caused by pathogenic fungi as agricultural or horticultural fungicides.

The compounds of the formula (I) of this invention may be effectively employed as fungicides against Archimycetes, Phycomycetes, Ascomycetes, Basidiomycetes, Fungi Imperfecti etc. as well as various plant diseases caused by other bacteria.

When used as agricultural or horticultural fungicides the compounds of this invention may be diluted directly with water or processed, by addition of agriculturally acceptable adjuvants, into various preparations using methods commonly employed in the field of producing agricultural chemicals. These various preparations may be used as such or after diluting with water to the desired concentration on actual use.

The agriculturally acceptable adjuvants which are herein referred to include, for example, diluents (solvents, fillers and carriers), surfactants (solubilizers, emulsifiers, dispersants and speaders), stabilizers, stickers, propellants for aerosols and synergists.

Examples of the solvents are water; and organic solvents, for example, hydrocarbons [as n-hexane, petroleum ether, naphtha, petroleum fractions (paraffin wax, kerosene, gas oil, middle oil, heavy oil etc.,), benzene, toluene, xylenes, etc.], halogenated hydrocarbons [such as chloromethylene, carbon tetrachloride, trichloroethylene, ethylene, chloride, ethylene dibromide, chlorobenzene, chloroform, etc.], alcohols [such as methyl alcohol, ethyl alcohol, propyl alcohol, ethylene glycol, etc.], ethers [such as diethyl ether, ethylene oxide, dioxane, etc.], alcohol ethers [such as ethylene glycol monomethyl ether, etc.], ketones [such as acetone, isophorone, etc.], esters [such as ethyl acetate, amyl acetate, etc.], amides [such as dimethylformamide, dimethylacetamide, etc.], sulfoxides [such as dimethylsulfoxide, etc.], and the like.

Examples of the fillers or carriers include organic pulverulent solids such as slaked lime, magnesium lime, gypsum, calcium carbonate, silica, perlite, pumice, calcite, diatomite, amorphous silicon dioxide, alumina, zeolite, clay minerals (such as pyrophyllite, talc, montmorillonite, beidellite, vermiculite, kaolinite, mica, etc.); vegetable pulverulent solids (such as cereal powders, starches, processed starches, sugar, glucose, plant stem crushed products, etc.); synthetic resin pulverulent solids (such as phenolic resins, urea resins, vinyl chloride resins, etc.), and the like.

Examples of the surfactants include anionic surfactants such as alkylsulfates (e.g. sodium laurylsulfate), arylsulfonic acids (e.g. alkylarylsulfonate salts, sodium alkylnaphthalenesulfonate, etc.), succinic acid salts, polyethylene glycol alkyl aryl ether sulfuric acid ester salts.; cationic surfactants such as alkylamines (e.g. laurylamine, stearyltrimethylammonium chloride, alkyldimethylbenzylammonium chloride, etc.), polyoxyethyleme alkylamines, etc.; nonionic surfactants such as polyoxyethylene glycol ethers (e.g. polyoxyethylene alkyl aryl ether and its condensates, etc.), polyoxyethylene glycol esters (e.g. polyoxyethylene fatty acid esters, etc.), polyol esters (e.g. polyoxyethylene sorbitan monolaurate, etc.), ampholytic surfactants and so forth.

Examples of other adjuvants are stabilizers, stickers [e.g. agricultural soaps, casein lime, sodium arginate, polyvinyl alcohol (PVA), vinyl acetate based adhesives, acrylic adhesives, etc.], propellants for aerosols [such as trichlorofluoromethane, dichlorofluoromethane, 1,2,2-trichloro-1,1,2-trifluoroethane, chlorobenzene, LNG, lower ethers, etc.]; combustion modifiers (for fumigation) [such as nitrites, zinc dust, dicyandiamide, etc.]; effect-prolonging agents; dispersion stabilizers [such as casein, tragacanth, carboxymethyl cellulose (CMC), polyvinyl alcohol (PVA), etc.]; and synergists.

The compounds of this invention may be formulated into various preparation forms using methods commonly employed in the field of producing agricultural chemicals. Examples of the preparation forms include emulsifiable concentrates, oil preparations, wettable powders, aqueous solutions, suspensions, powders, granules, pulverulent compositions, fumigants, tablets, aerosols, pastes, capsules, etc.

The agricultural or horticultural fungicides of this invention can contain the aforesaid active ingredients in amounts of about 0.1—about 95% by weight, preferably about 0.5—about 90% by weight.

In actual use, the active compound levels in the aforesaid various preparations and ready-to-use preparations can be appropriately varied, for example, in the range of about 0.0001—about 20% by weight, preferably about 0.005—about 10% by weight.

The levels of these active ingredients may be appropriately changed depending on the form of the preparation, the method, purpose, time and place of application, the severity of the crop diseases, etc.

The compounds of this invention may, if necessary, be used in the co-presence of other agricultural chemicals, such as insecticides, fungicides, acaricides, nematocides, antiviral agents, herbicides, plant growth regulators, and attractants [for example, organic phosphate compounds, carbamate compounds, dithio (or thiol) carbamate compounds, organic chlorine compounds, dinitro compounds, organic sulfur or metal compounds, antibiotics, substituted diphenyl ether compounds, urea compounds, triazine compounds, etc.], or/and fertilizers and the like.

The various preparations or ready-to-use preparations containing the aforesaid active ingredients according to this invention can be applied using a common application method such as spraying [for example, liquid spraying, misting, atomizing, dusting, granule-scattering, water surface application, pouring, etc.]; fumigation; soil application [for example, incorporating, sprinkling, vaporing, infusion, etc.]; surface application [for example, coating, banding, powder coating, covering, etc.]; impregnation, and the like. In addition they can also be used by the so-called ultra-low-volume method. In this method, it is possible for the composition to comprise even 100% of the active ingredient.

The dosage applied per unit area is about 0.03—about 10 kg, preferably about 0.3—about 6 kg, calculated as the active compound, per hectare. However, in special cases, it is possible or even sometimes necessary to apply a dosage higher or lower than the above range.

This invention provides agricultural or horticultural fungicidal compositions which comprise the active compounds of the above formula (I) as active ingredients and diluents (solvents and/or fillers and/or carriers) and/or sufactants, and, if necessary, e.g. stabilizers, stickers and synergists.

Further this invention also provides a method for controlling crop diseases which comprises applying compound of the above formula (I) either alone or in admixture with a diluent (solvent and/or filler and/or carrier) and/or surfactant, and, if necessary, e.g. a stabilizer, a sticker and a synergist.

This invention is more particularly described by the following examples but this invention should in no way be restricted thereto.

A. PREPARATIVE EXAMPLES

EXAMPLE 1

Example of Synthesis of Compound of Formula (II) of Invention

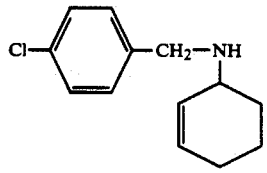

(Compound No. II-1)

35 g of 4-chlorobenzylamine was dissolved in 250 ml of toluene and, while stirring the solution with ice-cooling, a solution of 20 g of 3-bromocyclohexene in 20 ml of toluene was added dropwise. After the addition, the temperature was gradually raised, and stirring was further continued at 50° C. for about 5 hours. After cooling, the reaction mixture was filtered by suction, and the toluene layer was washed thoroughly with water. The toluene solution was dried on anhydrous sodium sulfate, the toluene was distilled off, and the residue was distilled under reduced pressure to obtain 15 g of the desired product, N-4-chlorobenzyl-2-cyclohexen-1-ylamine.

b.p. 134°–138° C./0.55 mm Hg.

The compounds of the formula (II) (intermediates) of this invention synthesized by procedures similar to those in Example 1 are given in Table 1.

TABLE 1

| Compound No. | Compound of Formula (II) of Invention (Intermediate) |
| --- | --- |
| II-2 | N-4-Chlorobenzyl-2-cyclopentenylamine b.p. 134–137° C./1.2 mm Hg |
| II-3 | N-4-Bromobenzyl-2-cyclopentenylamine b.p. 147–152° C./1.5 mmHg |
| II-4 | N-4-Methylbenzyl-2-cyclopentenylamine b.p. 120–121° C./1.5 mmHg |
| II-5 | N-4-Methylbenzyl-2-cyclohexenylamine b.p. 137–142° C./1.5 mm Hg |
| II-6 | N-4-Bromobenzyl-2-cyclohexenylamine b.p. 157–160° C./0.8 mm Hg |
| II-7 | N-4-Chlorobenzyl-3-cyclopentenylamine |
| II-8 | N-4-Bromobenzyl-3-cyclopentenylamine |
| II-9 | N-4-Chlorobenzyl-3-cyclohexenylamine |
| II-10 | N-4-Methylbenzyl-3-cyclohexenylamine |
| II-11 | N-4-Chlorobenzyl-2-cycloheptenylamine |

EXAMPLE 2

Example of Synthesis of Compound of Formula (I) of Invention

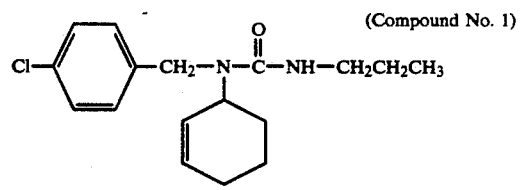

(Compound No. 1)

22 g of N-4-chlorobenzyl-2-cyclohexenylamine was dissolved in 400 ml of hexane and, while stirring the solution with ice-cooling, a solution of 9 g of propyl isocyanate in 30 ml of hexane was added dropwise. After the addition, the temperature was gradually raised, and stirring was further continued at 40° C. for about 3 hours. After cooling, the formed crystals were filtered off by suction, and recrystallized from a mixed solvent of hexane-ethyl alcohol to obtain 26.3 g of the desired product, 1-(4-chlorobenzyl)-1-(2-cyclohexenyl)-3-propylurea.

m.p. 80.0°–83.0° C.

EXAMPLE 3

Example of Synthesis of Compound of Formula (I) of Invention

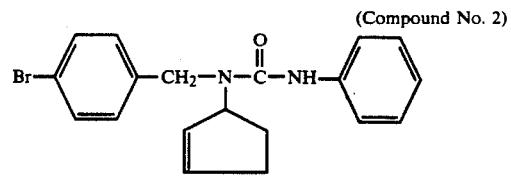

(Compound No. 2)

19 g of aniline was dissolved in 400 ml of toluene and, while stirring the solution with ice-cooling, a solution of 31 g of N-4-bromobenzyl-N-(2-cyclopentenyl)carbamoyl chloride in 50 ml of toluene was added dropwise. After the addition, the temperature was gradually raised, and stirring was further continued at 70°–80° C. for about 10 hours. After cooling, the crystallized aniline hydrochloride was filtered off, and the toluene layer was washed successively with water, a 1% aqueous sodium carbonate solution, a 1% aqueous hydrochloric acid and water. After washing, the toluene solution was dried on anhydrous sodium sulfate, the toluene was distilled off, and the residue was recrystallized from a mixed solvent of hexaneethyl alcohol to obtain 26.7 g of the desired product, 1-(4-bromobenzyl)-1-(2-cyclopentenyl)-3-phenylurea.

m.p. 106.0°–111.0° C.

The compounds of the formula (I) of this invention synthesized by procedures similar to those in Examples 2 and 3 are given in Table 2.

TABLE 2
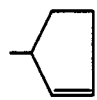
| Compound No. | X | R¹ | R² | Y | Physical constant mp. °C. |
|---|---|---|---|---|---|
| 3 | 4-Cl |  | —CH$_3$ | O | 82.0–88.0 |
| 4 | 4-Cl |  | —C$_2$H$_5$ | O | 88.5–90.5 |
| 5 | 4-Cl |  | —C$_3$H$_7$-n | O | 71.0–76.0 |
| 6 | 4-Cl |  | —C$_4$H$_9$-n | O | 53.0–55.5 |
| 7 | 4-Cl |  |  | O | 101.0–104.0 |
| 8 | 4-Cl |  |  | O | 110.0–111.5 |
| 9 | 4-Cl |  |  | O | 103.0–106.0 |
| 10 | 4-Br |  | —CH$_3$ | O | 74.0–76.0 |
| 11 | 4-Br | | —C$_2$H$_5$ | O | 83.0–86.0 |
| 12 | 4-Br | | —C$_3$H$_7$-iso | O | 63.0–68.0 |
| 13 | 4-CH$_3$ | | —C$_2$H$_5$ | O | 91.0–93.0 |
| 14 | 4-CH$_3$ | | —C$_3$H$_7$-n | O | 75.0–80.0 |

TABLE 2-continued $$X-\text{C}_6H_4-CH_2-N(R^1)-C(=Y)-NH-R^2$$

| Compound No. | X | R¹ | R² | Y | Physical constant mp. °C. |
|---|---|---|---|---|---|
| 15 | 4-CH₃ | cyclohexenyl | phenyl | O | 95.5–96.5 |
| 16 | 4-Cl | cyclohexenyl | —CH₃ | O | 105.0–106.0 |
| 17 | 4-Cl | cyclohexenyl | —C₂H₅ | O | 96.0–98.0 |
| 18 | 4-Cl | cyclohexenyl | —C₄H₉-n | O | 62.0–64.0 |
| 19 | 4-Cl | cyclohexenyl | cyclohexyl | O | 95.0–97.0 |
| 20 | 4-Cl | cyclohexenyl | phenyl | O | 131.5–132.5 |
| 21 | 4-Cl | cyclohexenyl | 2-OCH₃-phenyl | O | 92.0–96.0 |
| 22 | 4-Br | cyclohexenyl | —C₃H₇-n | O | 79.0–80.0 |
| 23 | 4-Br | cyclohexenyl | phenyl | O | 130.0–131.0 |
| 24 | 4-CH₃ | cyclohexenyl | —C₂H₅ | O | 68.0–71.0 |
| 25 | 4-CH₃ | cyclohexenyl | —C₃H₇-n | O | 59.0–63.0 |
| 26 | 4-CH₃ | cyclohexenyl | phenyl | O | 93.0–94.5 |

TABLE 2-continued

Structure: X—(phenyl)—CH₂—N(R¹)—C(=Y)—NH—R²

| Compound No. | X | R¹ | R² | Y | Physical constant mp. °C. |
|---|---|---|---|---|---|
| 27 | 4-CH₃ | 2-cyclohexenyl | 3-methoxyphenyl | O | 100.0–104.0 |
| 28 | 4-Cl | 2-cyclopentenyl | —C₂H₅ | S | 98.5–100.0 |
| 29 | 4-Cl | 2-cyclopentenyl | phenyl | S | 130.0–133.0 |
| 30 | 4-Br | 2-cyclopentenyl | —CH₂—phenyl | S | 111.0–118.0 |
| 31 | 4-Br | 2-cyclopentenyl | phenyl | S | 136.0–141.0 |
| 32 | 4-CH₃ | 2-cyclopentenyl | —C₄H₉-n | S | 52.0–54.0 |
| 33 | 4-Cl | 2-cyclohexenyl | —C₂H₅ | S | 96.0–97.5 |
| 34 | 4-Cl | 2-cyclohexenyl | phenyl | S | 129.0–132.5 |
| 35 | 4-CH₃ | 2-cyclohexenyl | —C₂H₅ | S | 87.5–88.5 |

Further, the following compounds of the formula (I) of this invention were synthesized by procedures similar to those in Example 2:

1-(4-chlorobenzyl)-1-(2-cyclopentenyl)-3-(3-hydroxyphenyl) urea,
1-(4-chlorobenzyl)-1-(2-cyclohexenyl)-3-(4-hydroxyphenyl) urea,
1-(4-chlorobenzyl)-1-(2-cyclohexenyl)-3-(4-methoxyphenyl) urea,
1-(4-chlorobenzyl)-1-(3-cyclopentenyl)-3-phenylurea,
1-(4-chlorobenzyl)-1-(3-cyclohexenyl)-3-propylurea,
1-(4-chlorobenzyl)-1-(2-cycloheptenyl)-3-phenylurea.

The preparations of the compounds of this invention and the biological tests on them are specifically illustrated by the following examples. Compound Nos. correspond to the above.

B. FORMULATION EXAMPLES

EXAMPLE 4

Wettable Powder

15 Parts of Compound No. 1 of this invention, 80 parts of a 1:5 mixture of powdered diatomite and powdered clay, 2 parts of sodium alkylbenzenesulfonate and 3 parts of a condensate of sodium alkylnaphthalenesulfonate and formalin were ground and mixed together to prepare a wettable powder. It is diluted with water and applied by spraying to pathogenic fungi and/or sites where they are breeding and crop diseases were broken out.

EXAMPLE 5

Emulsifiable Concentrate

30 Parts of Compound No. 2 of this invention, 55 parts of xylene, 8 parts of polyoxyethylene alkyl phenyl ether and 7 parts of calcium alkylbenzenesulfonate were mixed with stirring to prepare an emulsifiable concentrate. It is diluted with water and applied by spraying to pathogenic fungi and/or sites where they are breeding and crop diseases were broken out.

EXAMPLE 6

Dust

2 Parts of Compound No. 3 of this invention and 98 parts of powdered clay were ground and mixed together to prepare a dust. It is dusted over pathogenic fungi and/or sites where they are breeding and crop diseases were broken out.

EXAMPLE 7

Dust 1.5 Parts of Compound No. 4 of this invention, 0.5 part of isopropyl hydrogen phosphate (PAP) and 98 parts of powdered clay were ground and mixed together to prepare a dust. It is dusted over pathogenic fungi and/or sites where they are breeding and crop diseases were broken out.

EXAMPLE 8

Granules

25 Parts of water were added to a mixture of 10 parts of Compound No. 5 of this invention, 30 parts of bentonite (montmorillonite), 58 parts of talc and 2 parts of lignin sulfonate, intimately kneaded and pelletized using an extruding granulator to obtain granules of 10-40 mesh, which were then dried at 40°-50° C. to prepare granules. They are applied by scattering to pathogenic fungi and/or sites where they are breeding and crop diseases were broken out.

EXAMPLE 9

Granules

95 Parts of clay material particles having a particle size distribution of 0.2-2 mm were charged into a rotary mixer and 5 parts of Compound No. 6 dissolved in an organic solvent was sprayed over it while rotating to be uniformly absorbed, thereby preparing granules. They are applied by scattering to pathogenic fungi and/or sites where they are breeding and crop diseases were broken out.

EXAMPLE 10

Oil Preparation 0.5 Part of Compound No. 7 of this invention and 99.5 parts of kerosene were mixed with stirring to prepare an oil preparation. This is applied by spraying to pathogenic fungi and/or sites where they are breeding and crop diseases were broken out.

C. USE EXAMPLES

EXAMPLE 11

Test on Effect to Control Pellicularia sasakii by Spraying (Pot Test)

Preparation of Test Formulations

| Active Compound: | 50 parts by weight, |
|---|---|
| Carrier: | 45 parts by weight of a 1:5 mixture of diatomite and kaolin, |
| Emulsifier: | 5 parts by weight of polyoxyethylene alkyl phenyl ether. |

The above active compound, carrier and emulsifier in amounts specified above were ground and mixed to prepare a wettable powder, and a predetermined amount thereof was diluted with water to prepare a formulation.

TESTING METHOD

Rice plants (variety:Kinmaze) were grown in Wagner pots of 1 a/5000 under the full water conditions, and at the young ear formation stage, the formulation of the active compound prepared above and diluted to the predetermined concentration was sprayed at a rate of 100 ml per 3 pots. The following day, the test rice plants were inoculated at the bottom of stems with Pellicularia sasakii which had been cultured in a barely medium for 10 days to form sclerotia, and allowed to become infected by maintaining them in a wet chamber at 28°-30° C. and a relative humidity of 95% or higher for 10 days, after which the degree of attack and the presence of phytotoxicity were examined. The examination was done by measuring the expansion of the lesion from the inoculation site and the degree damage was expressed by the following standard:

$$\text{Degree of Damage} = \frac{3n_3 + 2n_2 + n_1 + n_0}{3N} \times 100$$

wherein
N: Total number of the examined stems
$n_0$: Number of stems free from infection
$n_1$: Number of stems infected up to the first-leaf leave sheath (from bottom)
$n_2$: Number of stems infected up to the second-leaf leave sheath (from bottom)
$n_3$: Number of stems infected up to the third-leaf leave sheath or above (from bottom)

In this test, a clearly superior activity compared with the prior art is shown, for example, by Compounds Nos. 1, 2, 5, 6, 7, 8, 9, 15, 16, 17, 18, 19, 20, 21, 22, 23, 26, 27, 29, 31, 33 and 34.

TABLE 3

| Compound No. | Concentration of Active Ingredient ppm | Degree of Damage % | Phytotoxicity |
|---|---|---|---|
| 1 | 50 | 0 | — |
| 2 | 50 | 0 | — |
| 5 | 50 | 0 | — |
| 6 | 250 | 0 | — |
| 7 | 250 | 0 | — |
| 8 | 50 | 0 | — |
| 9 | 250 | 0 | — |
| 15 | 50 | 0 | — |
| 16 | 250 | 0 | — |
| 17 | 50 | 0 | — |
| 18 | 50 | 0 | — |

TABLE 3-continued

| Compound No. | Concentration of Active Ingredient ppm | Degree of Damage % | Phytotoxicity |
|---|---|---|---|
| 19 | 50 | 0 | — |
| 20 | 50 | 0 | — |
| 21 | 50 | 0 | — |
| 22 | 50 | 0 | — |
| 23 | 50 | 0 | — |
| 26 | 50 | 0 | — |
| 27 | 50 | 0 | — |
| 29 | 50 | 0 | — |
| 31 | 50 | 0 | — |
| 33 | 250 | 0 | — |
| 34 | 50 | 0 | — |
| X-1 (Comparative Compound) | 250 | 80.5 | — |
| X-2 (Comparative Compound) | 250 | 80.0 | — |
| X-3 (Comparative Compound) | 250 | 73.5 | — |
| polyoxin (Commercial Product Control) | 45 | 22.5 | — |
| validamycin A (Commercial Product Control) | 60 | 15 | — |
| No Treatment | | 81.5 | |

Notes:
1) X-1 (Comparative Compound)

(Compound described in U.S. Pat. No. 3,701,807 specification)
X-2 (Comparative Compound)

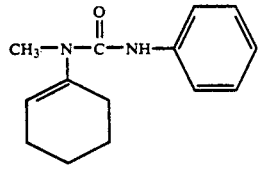

(Same as above)
X-3 (Comparative Compound)

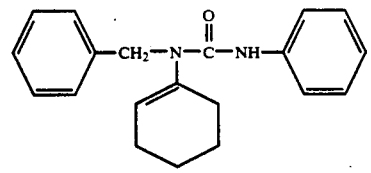

(Compound falling in the scope of the general formula described in U.S. Pat. No. 3,701,807 specification)
polyoxin: polyoxin compound zinc salt (2.2% liquid preparation of polyoxin D-Zn)
validamycin A: 3% liquid preparation of validamycin A
2) In the table, the "—" in the Phytotoxicity column means the absence of phytotoxicity.

EXAMPLE 12

Test on Effect to Control Rhizoctonia solani (in Greenhouse)

This example shows the results of the test on the effect to controlling soil-borne causative pathogenic fungi, Rhizoctonia solani which causes damping-off of seedlings of various crop plants by soil treatment.

Preparation of Test Formulations

3 Parts by weight of the active compound and 97 parts by weight of talc were ground and mixed together.

Testing Method

Infected soil was prepared by inoculating field soil (clay loam) which had been sterilized in an autoclave, with Rhizoctonia solani which has been cultured in a wheat bran medium for 10 days, and the dust preparation prepared above was incorporated into the soil to the predetermined concentration and well stirred to treat it. This chemical-treated soil and non-treated soil for comparison were packed into plastic containers of $27 \times 18$ cm$^2$ in area and 9 cm in depth to make nurseries respectively, then seeds of cucumber and egg plant were sown in each box, 50 seeds per box, allowed to germinate by maintaining in usual manner in a greenhouse, and the number of the infected seedings and the phytotoxicity to the germination and growth were assessed at the predetermined intervals. According to the test results on the day 25, Compounds Nos. 1, 2, 20, 23 and 26 manifested a controlling effect of nearly 100% against damping-off of cucumber and egg plant at a concentration of the active ingredient of 25 ppm.

It will be understood that the specification and examples are illustrative but not limitative of the present invention and that other embodiments within the spirit and scope of the invention will suggest themselves to those skilled in the art.

What is claimed is:

1. A substituted benzylcycloalkenylamine of the formula

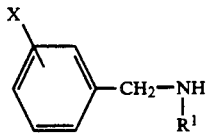

in which
X is chlorine, bromine or methyl, and
R$^1$ is 2-cyclopentenyl or 2-cyclohexenyl.
2. A compound according to claim 1, wherein such compound is N-4-chlorobenzyl-2-cyclopenten-1-ylamine.
3. A compound according to claim 1, wherein such compound is N-4-bromobenzyl-2-cyclopenten-1-ylamine.
4. A compound according to claim 1, wherein such compound is N-4-methylbenzyl-2-cyclopenten-1-ylamine.
5. A compound according to claim 1, wherein such compound is N-4-chlorobenzyl-2-cyclohexen-1-ylamine.
6. A compound according to claim 1, wherein such compound is N-4-bromobenzyl-2-cyclohexen-1-ylamine.
7. A compound according to claim 1, wherein such compound is N-4-methylbenzyl-2-cyclohexen-1-ylamine.
8. A compound according to claim 1, wherein such compound is N-4-chlorobenzyl-3-cyclopenten-1-ylamine.
9. A compound according to claim 1, wherein such compound is N-4-bromobenzyl-3-cyclopenten-1-ylamine.
10. A compound according to claim 1, wherein such compound is N-4-chlorobenzyl-3-cyclohexen-1-ylamine.
11. A compound according to claim 1, wherein such compound is N-4-methylbenzyl-3-cyclohexen-1-ylamine.

* * * * *